United States Patent
Ivie et al.

(10) Patent No.: US 8,420,116 B2
(45) Date of Patent: Apr. 16, 2013

(54) DIETARY COMPOSITIONS FOR PROMOTING WEIGHT LOSS

(75) Inventors: Jeremy Ivie, Ammon, ID (US); Jennifer Kelsey, Ririe, ID (US); Alexander B. Rabovsky, Idaho Falls, ID (US)

(73) Assignee: Melaleuca, Inc., Idaho Falls, ID (US)

( * ) Notice: Subject to any disclaimer, the term of this patent is extended or adjusted under 35 U.S.C. 154(b) by 0 days.

(21) Appl. No.: 13/050,631

(22) Filed: Mar. 17, 2011

(65) Prior Publication Data

US 2011/0165313 A1    Jul. 7, 2011

Related U.S. Application Data

(63) Continuation of application No. 12/348,232, filed on Jan. 2, 2009, now abandoned.

(60) Provisional application No. 61/018,812, filed on Jan. 3, 2008.

(51) Int. Cl.
*A61K 47/00* (2006.01)
*A23L 1/30* (2006.01)

(52) U.S. Cl.
USPC ......................... 424/439; 426/648

(58) Field of Classification Search .................. None
See application file for complete search history.

(56) References Cited

U.S. PATENT DOCUMENTS

| | | | |
|---|---|---|---|
| 6,686,456 B2 | 2/2004 | Ausich et al. | |
| 6,767,566 B2 | 7/2004 | Ausich et al. | |
| 6,827,954 B2 | 12/2004 | Prosise et al. | |
| 6,872,544 B2 | 3/2005 | Stomp et al. | |
| 2004/0087514 A1 | 5/2004 | Hughes et al. | |
| 2004/0258829 A1* | 12/2004 | Zheng et al. | 426/615 |
| 2005/0008754 A1 | 1/2005 | Sweeney et al. | |
| 2005/0260302 A1* | 11/2005 | Prosise | 426/72 |
| 2006/0094693 A1 | 5/2006 | Aziz et al. | |
| 2006/0100171 A1 | 5/2006 | Ekhart et al. | |
| 2006/0204567 A1* | 9/2006 | Hu et al. | 424/451 |
| 2007/0087084 A1 | 4/2007 | Edward et al. | |
| 2008/0311265 A1* | 12/2008 | MacDonald et al. | 426/534 |

OTHER PUBLICATIONS

Authorized Officer Kee-Yeun Kim, International Search Report/Written Opinion, PCT/US2009/030042 mailed Mar. 13, 2009, 11 pages.
Authorized Examiner Athina Nickitas-Etienee, International Preliminary Report on Patentability for PCT/US2009/030042, mailed Jul. 15, 2010, 6 pages.

* cited by examiner

*Primary Examiner* — Daniel Sullivan
*Assistant Examiner* — Melissa Javier
(74) *Attorney, Agent, or Firm* — Fish & Richardson P.C.

(57) ABSTRACT

Dietary compositions for enhancing feelings of satiety and thereby enhancing weight loss are disclosed herein. For example, dietary compositions containing a combination of beta glucan, whey protein, a natural protein extract derived from potatoes, and optionally inulin are provided.

18 Claims, No Drawings

DIETARY COMPOSITIONS FOR PROMOTING WEIGHT LOSS

CROSS-REFERENCE TO RELATED APPLICATIONS

This application is a continuation of U.S. patent application Ser. No. 12/348,232, filed Jan. 2, 2009, entitled "Dietary Compositions for Promoting Weight Loss," which claims the benefit of U.S. Provisional Application No. 61/018,812, entitled "Dietary Compositions" and filed on Jan. 3, 2008, which are incorporated herein by reference in their entirety.

BACKGROUND

1. Technical Field

This disclosure relates to dietary compositions that can aid in weight loss efforts. In particular, this disclosure provides dietary compositions containing a natural protein extract derived from potatoes, a beta glucan source, a dairy protein source, and optionally inulin.

2. The Relevant Technology

The population of people considered "overweight" has reached epidemic levels, which not only increases the risk of disease in those individuals, but also puts a strain on the healthcare industry as a whole. In fact, obesity is considered by some health authorities to be a leading cause of disease throughout the world, and particularly the United States. One approach to combating obesity is through the administration of healthy dietary compositions. Dietary compositions for combating weight gain and obesity can include foods, medicinal ingredients, extracts, herbs, and other forms of matter that can be ingested or otherwise absorbed by some part of the human body.

BRIEF SUMMARY

This disclosure provides dietary compositions configured to enhance weight loss efforts and increase health by increasing satiety in a user consuming the dietary composition. The disclosed dietary compositions increase satiety by both increasing the physical feeling of fullness in the stomach (over and above that caused by the volume of food consumed) and simultaneously promoting the release of cholecystokinin (CCK), a hormone that reduces hunger in the consumer. A user consuming the provided dietary composition in conjunction with a carrier food source (e.g. a shake, bar, or soup), or an additional food, will perceive feelings of satiety above that which would be perceived in the absence of the herein provided dietary compositions.

In certain embodiments, the dietary compositions contain a natural protein extract derived from potatoes, beta glucan, a dairy protein source such as whey protein, and optionally inulin. In some cases, a dietary composition provided herein can include SLENDESTA™ brand protein extract, oat beta glucan, barley beta glucan, inulin, and whey protein isolate.

In general, one aspect of this document features a dietary composition comprising oat beta glucan, barley beta glucan, inulin, whey protein, and a natural protein extract derived from potatoes. The protein extract can be present from about 2 percent to about 14 percent by weight. The oat beta glucan can be present from about 2 percent to about 50 percent by weight. The barley beta glucan can be present from about 2 percent to about 50 percent by weight. The inulin can be present from about 2 percent to about 50 percent by weight. The whey protein can be present from about 5 percent to about 50 percent by weight. The dietary composition can be a pill, a powder, or a liquid.

In another aspect, this document features a dietary composition consisting of between 15 and 300 mg of potato protein extract, between 10 and 1250 mg of oat beta glucan, between 10 and 1250 mg of barley beta glucan, between 50 and 1250 mg of inulin, and between 125 and 1250 mg of a dairy protein source such as, without limitation, whey protein isolate (WPI). In another aspect, this document features a dietary composition consisting essentially of between 15 and 300 mg of potato protein extract, between 10 and 1250 mg of oat beta glucan, between 10 and 1250 mg of barley beta glucan, between 50 and 1250 mg of inulin, and between 125 and 1250 mg of a dairy protein source such as, without limitation, WPI.

In another aspect, this document features a dietary composition consisting of between about 2 percent to about 14 percent by weight potato protein extract, 2 percent to about 50 percent by weight oat beta glucan, 2 percent to about 50 percent by weight barley beta glucan, 2 percent to about 50 percent by weight inulin, and 5 percent to about 50 percent by weight diary protein source such as, without limitation, WPI. In another aspect, this document features a dietary composition consisting essentially of between about 2 percent to about 14 percent by weight potato protein extract, 2 percent to about 50 percent by weight oat beta glucan, 2 percent to about 50 percent by weight barley beta glucan, 2 percent to about 50 percent by weight inulin, and 5 percent to about 50 percent by weight diary protein source such as, without limitation, WPI.

Unless otherwise defined, all technical and scientific terms used herein have the same meaning as commonly understood by one of ordinary skill in the art to which this disclosure pertains. Although methods and materials similar or equivalent to those described herein can be used in the practice or testing, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments are set forth in and the description below. Other features, objects, and advantages will be apparent from the detailed description, and from the claims.

DETAILED DESCRIPTION OF CERTAIN EMBODIMENTS

In general, this disclosure provides dietary compositions configured to enhance weight loss efforts by increasing satiety in a user consuming the dietary composition. The disclosed dietary compositions increase satiety by increasing the physical feeling of fullness in the stomach (over and above that normally caused by the volume of food consumed) and simultaneously directly providing peptides and promoting the release of peptides that reduce hunger in the consumer and otherwise stimulate feelings of fullness. For example, this disclosure provides dietary compositions containing a natural protein extract derived from potatoes, beta glucan, a dairy protein source such as whey protein, and optionally inulin.

With reference to the specific ingredients for use in the disclosed dietary compositions, any form of a natural protein extract derived from potatoes can be included. The potato protein extract preferably includes as its active component Proteinase Inhibitor II (PI2). Although the present invention is not limited by any particular theory, PI2 is believed to promote the release of CCK, a natural signaling peptide within a human body. Once released, CCK can travel through the blood targeting various organs, where it induces feelings of fullness and satisfaction, i.e., satiety. One non-limiting source of the natural protein extract is SLENDESTA™, a natural satiety ingredient for weight loss that is derived from white potatoes and sold by Kemin Industries, Inc. under the trademark SLENDESTA™. SLENDESTA™ is potato protein extract can be standardized to its active component Proteinase Inhibitor II (PI2). Further details regarding SLENDESTA™ can be found in U.S. Pat. Nos. 6,872,544, 6,767,566, and 6,686,456, each of which is incorporated herein by reference.

A dietary composition provided herein can contain any amount of the natural protein extract derived from potatoes. For example, a dietary composition can contain from about 0.01 µg to about 0.06 g (e.g., from about 0.01 µg to about 50 mg; from about 0.01 µg to about 10 mg; from about 0.01 µg to about 1 mg; from about 0.01 µg to about 750 µg; from about 0.01 µg to about 500 µg; from about 0.1 µg to about 60 mg; from about 1 µg to about 60 mg; from about 100 µg to about 60 mg; from about 500 µg to about 60 mg; or from about 1 mg to about 50 mg) of SLENDESTA™ or other natural protein extract derived from potatoes. In some cases, a dietary composition can contain about 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100 mg or more of a natural protein extract derived from potatoes, about any amount of a natural protein extract derived from potatoes between these enumerated amounts, or any range of amounts of a natural protein extract derived from potatoes encompassing one or more of these enumerated amounts (e.g., from about one of the enumerated amounts of natural protein extract derived from potatoes to about another of the enumerated amounts of natural protein extract derived from potatoes). In some cases, between about 0.00001 percent to about 35 percent (e.g., between about 0.00001 percent and about 30 percent; between about 0.00001 percent and about 25 percent; between about 0.00001 percent and about 10 percent; between about 0.00001 percent and about 5 percent; between about 0.001 percent and about 30 percent; between about 0.1 percent and about 30 percent; between about 1 percent and about 30 percent; or between about 1 percent and about 5 percent) of a dietary composition can be a natural protein extract derived from potatoes. In some cases, a dietary composition can contain about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 30, 35, 40, 45, 50 percent or more of a natural protein extract derived from potatoes, about any percentage of a natural protein extract derived from potatoes between these enumerated percentages, or any range of percentages of a natural protein extract derived from potatoes encompassing one or more of these enumerated percentages (e.g., from about one of the enumerated percentages of natural protein extract derived from potatoes to about another of the enumerated percentages of natural protein extract derived from potatoes).

In certain embodiments, dietary compositions provided herein also include beta glucan. Beta-glucan is a natural polysaccharide made of glucose. For example, a dietary composition can include oat beta glucan. Oat beta glucan can increase the viscosity of stomach contents, which can slow stomach emptying, prolong the absorption of energy from a meal, and decrease the absorption of fat. These effects can exert strong control over insulin release in the body, which can reduce cholesterol production, extend satiety, and benefit heart and glycemic health. Any type of beta glucan can be included in a dietary composition provided herein. Examples of beta glucan include, without limitation, oat, barley, wheat, and other beta glucans. Beta glucan can be in any form, for example, a solution, a powder, or a soluble powder.

A dietary composition provided herein can contain any number of different beta glucans. For example, a dietary composition can contain one, two, three, four, five, six, seven, eight, nine, ten, or more different beta glucans. Any appropriate method can be used to obtain beta glucans. For example, water can be used to obtain a preparation of beta glucan. In some cases, beta glucan can be extracted from naturally-occurring sources. A dietary composition provided herein can contain any amount of a beta glucan. For example, a dietary composition can contain from about 0.01 µg to about 5 g (e.g., from about 0.01 µg to about 5 g; from about 0.01 µg to about 2.5 g; from about 0.01 µg to about 1 g; from about 0.01 µg to about 750 mg; from about 0.01 µg to about 500 mg; from about 0.1 µg to about 1 g; or from about 1 µg to about 500 mg) of beta glucan. In some cases, a dietary composition can contain about 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100, 200, 300, 400, 500, 600, 700, 800, 900, 1000, 1500, 2000, 2500 mg or more of beta glucan, about any amount of beta glucan between these enumerated amounts, or any range of beta glucan amounts encompassing one or more of these enumerated amounts (e.g., from about one of the enumerated amounts of beta glucan to about another of the enumerated amounts of beta glucan). In some cases, between about 0.2 percent to about 70 percent (e.g., between about 0.2 percent to about 60 percent; between about 0.2 percent to about 50 percent; between about 0.2 percent to about 250 percent; between about 0.5 percent to about 70 percent; between about 1 percent to about 70 percent; between about 5 percent to about 70 percent; between about 0.5 percent to about 50 percent; between about 1 percent to about 60 percent; or between about 1 percent to about 50 percent) of a dietary composition can be beta glucan. In some cases, a dietary composition can contain about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75 percent or more of beta glucan, about any percentage of beta glucan between these enumerated percentages, or any range of beta glucan percentages encompassing one or more of these enumerated percentages (e.g., from about one of the enumerated percentages of beta glucan to about another of the enumerated percentages of beta glucan).

In some cases, OATVANTAGE™ oat bran concentrate (an all natural, highly concentrated oat soluble fiber, containing 54% beta-glucan, 18 times more beta-glucan than regular oats) can be used in a dietary composition provided herein. In contrast with starch, which is alpha-1,4-glucan, this is a polymer made of (1,3),(1,4)-beta-connected glucose molecules.

In certain embodiments, dietary compositions provided herein include dairy protein source such as, without limitation, whey protein. For example, whey protein isolate (WPI) is a highly purified, natural source of whey protein that can be incorporated into a dietary composition provided herein. WPI can contain high levels of glycomacropeptides, biologically active peptides that can stimulate the feeling of fullness. Any type of whey protein can be included in a dietary composition provided herein. Whey protein can be in any form, for example, a solution, a powder, or a soluble powder.

A dietary composition provided herein can contain any number of different types of whey protein. For example, a dietary composition can contain one, two, three, four, five, six, seven, eight, nine, ten, or more different types of whey protein. Exemplary types of whey protein include PROVON™ 190/192, PROVON™ 190HS, PROVON™ A-190, and PROVON™ 290/292, available from Glanbia Nutritionals. Any appropriate method can be used to obtain whey protein. For example, milk can be used to obtain a preparation of whey protein. In some cases, whey protein can be concentrated and filtered from milk or other dairy sources. In some cases, an isolation process can be performed using fluid milk as a source material to obtain a preparation of WPI. A dietary composition provided herein can contain any amount of whey protein. For example, a dietary composition can contain from about 0.01 µg to about 10 g (e.g., from about 0.01 µg to about 8 g; from about 0.01 µg to about 5 g; from about 0.1 µg to about 10 g; from about 1 µg to about 10 g; from about 10 µg to about 10 g; from about 100 µg to about 10 g; from about 1 mg to about 10 g; or from about 10 mg to about 5 g) of whey protein (e.g., PROVON™). In some cases, a dietary composition can contain about 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100, 200, 300, 400, 500, 600, 700, 800, 900, 1000, 1500, 2000, 2500 mg or more of whey protein, about any amount of whey protein between these enumerated amounts, or any range of whey protein amounts encompassing one or more of these enumerated amounts (e.g., from about one of the enumerated amounts of whey protein to about another of the enumerated amounts of whey protein). In some cases, between about 0.01 percent to about 30 percent (e.g., between about 0.01 percent and to about 25 percent; between about 0.01 percent and to about 20 percent; between about 0.01 percent and to about 15 percent; between about 0.1 percent and to about 25 percent; between about 1 percent and to about 25 percent; between about 5 percent and to about 25 percent; between about 0.1 percent and to about 20 percent; or between about 1 percent and to about 20 percent) of a dietary composition can be whey protein (e.g., PROVON™). In some cases, a dietary composition can contain about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80 percent or more of whey protein, about any percentage of whey protein between these enumerated percentages, or any range of whey protein percentages encompassing one or more of these enumerated percentages (e.g., from about one of the enumerated percentages of whey protein to about another of the enumerated percentages of whey protein).

In some cases, a dietary composition provided herein can include optional ingredients such as inulin. Inulin is a group of polysaccharides produced by many types of plants or synthetically created. Inulin can increase fiber content and slowing the stomach emptying process. Any type of inulin can be included in a dietary composition provided herein. Examples of inulin include, without limitation, short, medium, and long chain inulin. Inulin can be in any form, for example, a solution, a powder, or a soluble powder.

A dietary composition provided herein can contain any number of different inulins. For example, a dietary composition can contain one, two, three, four, five, six, seven, eight, nine, ten, or more different inulins. Any appropriate method can be used to obtain an inulin. For example, extraction can be used to obtain a preparation of inulins. In some cases, inulin can be extracted from naturally-occurring sources, such as plants. In particular, the chicory or Jerusalem artichoke plants can be used as a source of inulin. In some cases, a water extraction process can be performed using chicory as a source material to obtain a preparation of inulin. A dietary composition provided herein can contain any amount of an inulin. For example, a dietary composition can contain from about 0.01 µg to about 8 g (e.g., from about 0.01 µg to about 6 g; from about 0.01 µg to about 5 g; from about 0.1 µg to about 8 g; from about 1 µg to about 8 g; from about 10 µg to about 8 g; from about 100 µg to about 8 g; from about 1 mg to about 8 g; or from about 10 mg to about 5 g) of inulin. In some cases, a dietary composition can contain about 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100, 200, 300, 400, 500, 600, 700, 800, 900, 1000, 1500, 2000, 2500 mg or more of inulin, about any amount of inulin between these enumerated amounts, or any range of inulin amounts encompassing one or more of these enumerated amounts (e.g., from about one of the enumerated amounts of inulin to about another of the enumerated amounts of inulin). In some cases, between about 0.01 percent to about 20 percent (e.g., between about 0.01 percent and to about 15 percent; between about 0.01 percent and to about 10 percent; between about 0.01 percent and to about 5 percent; between about 0.1 percent and to about 20 percent; between about 1 percent and to about 20 percent; between about 5 percent and to about 20 percent; between about 0.1 percent and to about 15 percent; or between about 1 percent and to about 15 percent) of a dietary composition can be inulin. In some cases, a dietary composition can contain about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, 50 percent or more of inulin, about any percentage of inulin between these enumerated percentages, or any range of inulin percentages encompassing one or more of these enumerated percentages (e.g., from about one of the enumerated percentages of inulin to about another of the enumerated percentages of inulin).

In some cases, a dietary composition provided herein can contain SLENDESTA™ (or other potato protein extract), oat and barley beta glucan, inulin, and PROVON™ (or other whey protein source). The weight ratio of SLENDESTA™ (or other potato protein extract) to other ingredients (e.g., oat and barley beta glucan, inulin, dairy protein, and other additives) can be from about 1 to about 6. The ratio can be based, for example, on the dry weight of each ingredient or extract.

In some cases, a dietary composition provided herein can be designed to contain the following per serving: 150 mg of SLENDESTA™ (or other potato protein extract), 100 mg of oat Beta Glucan, 650 mg of barley Beta Glucan, and 400 mg of WPI.

A dietary composition provided herein can be ingested. For example, a dietary composition can be administered orally or intragastrically. In some cases, a dietary composition provided herein can be administered by other routes such as nasally, intravenously, intramuscularly, subcutaneously, sublingually, intrathecally, or intradermally. Any amount of a dietary composition provided herein can be administered to a mammal. The dosages of a dietary composition can depend on many factors, including the mode of administration. The amount of SLENDESTA™ (or other potato protein extract), oat and barley beta glucan, inulin, and PROVON™ (or other whey protein source) contained within a single dose of a dietary composition can be an amount that can effectively maintain a desired result in a mammal without inducing significant toxicity. For example, a dietary composition can be formulated in a dose such that an individual receives from about 100 mg up to about 600 mg of SLENDESTA™ (or other potato protein extract), from about 10 mg up to about 750 mg of oat beta glucan, from about 10 mg up to about 750 mg of barley beta glucan, from about 100 mg up to about 7 g of inulin, from about 100 mg up to about 10 g of WPI, per serving. Typically, a dietary composition can be administered in an amount from about 600 mg up to about 15 g per serving.

A dietary composition provided herein can be in the form of a liquid, solution, suspension, pill, capsule, tablet, gel cap, powder, or gel. For oral administration, tablets or capsules can be prepared by conventional means with acceptable excipients such as binding agents, fillers, lubricants, disintegrants, or wetting agents. The tablets can be coated, if desired. Liquid preparations for oral administration can take the form of, for example, solutions, syrups, or suspension, or they can be presented as a dry product for constitution with saline or other suitable liquid vehicle before use. Dietary compositions of the type described herein also can contain acceptable additives as will be understood by one skilled in the art depending on the particular form of the dietary composition. Non-limiting examples of such additives include suspending agents, emulsifying agents, non-aqueous vehicles, preservatives, buffer salts, flavoring, coloring, and sweetening agents as appropriate. Non-limiting examples of specific additives include: gelatin, glycerin, water, beeswax, lecithin, cocoa, caramel, titanium dioxide, or carmine. Preparations for oral administration also can be suitably formulated to give controlled release of the ingredients.

In some cases, a dietary composition provided herein can contain an acceptable carrier for administration to a mammal (e.g., a human), including, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Acceptable carriers also can include physiologically acceptable aqueous vehicles (e.g., physiological saline) or other known carriers appropriate to specific routes of administration.

In some cases, the dietary composition can be included as a supplement in a carrier food form, for example in the form of a shake, bar, or soup. For example, a blend of ingredients provided herein can be incorporated into a base of soy crisps, syrups, sweeteners, and fiber sources to produce an extruded protein bar. In some cases, the product can be in the form of a chocolate bar (e.g., a chocolate protein bar) of substantially uniform consistency. The chocolate bar can be dark chocolate, light chocolate, white chocolate, any other type of chocolate, or a mixture thereof. For example, a dietary composition can be in the form of a dark chocolate bar. Dark chocolate is known to contain cacao, a substance known to contain over 300 identifiable compounds including protein, fiber, iron, zinc, copper, calcium, magnesium, and high levels of potent antioxidants. Optionally, caramel, peanut butter, or any of a variety of other flavorings or food products can be added to the bar. A bar can be, for example, about 50 grams in weight, and can provide one serving of pre-blend. A bar can be of greater or lesser weight (e.g., 25 or 100 grams), and can provide more or less and one serving of pre-blend (e.g. half a serving or two servings). The product can be coated or partially coated in chocolate (or other flavor), and each bar can be individually packaged. The product can be coated or partially coated in dark chocolate, light chocolate, any other type of chocolate, or a mixture thereof. The final product can be consumed as one serving as either a meal replacement or snack item.

In another example, a blend of ingredients provided herein can be added to a meal replacement shake base. The configuration of a suitable shake base is known in the art and will be apparent to one skilled in the art in view of the disclosure herein. The final shake can be any flavor (e.g., chocolate, vanilla, or strawberry). Final serving size can be, for example, 30 g to be dispersed into 8 ounces of milk or water (or other suitable liquid) to form one complete serving. Final serving size can be greater or lesser than 30 grams (e.g., 15 or 60 grams) and can provide more or less than one complete serving (e.g., half a serving or two servings).

In some cases, dietary compositions provided herein can be provided to a subject for ingestion as stand alone supplement forms, such as tablets or capsules, in addition to being provided as shakes or bars, to increase the amount of oat beta glucan, barley beta glucan, inulin, whey protein, natural protein extract derived from potatoes, or any other ingredients in the dietary composition consumed by the subject.

As described herein, a dietary composition can be used to aid in weight loss in a mammal. Weight loss can be examined using any appropriate method. For example, by using a weight scale. A human's weight can be continually or intermittently monitored over a period of time, e.g., once a day, once a week, once a month. A weight trend may indicate the effectiveness of a dietary composition in lowering a human's weight or maintaining a healthy weight.

The following examples further describe dietary compositions but do not limit the scope of the inventive concepts described in the claims.

EXAMPLES

Example 1

Dietary Composition Formulation

A powder mix was formed by blending SLENDESTA™ (6% by weight), oat beta glucan (7% by weight), barley beta glucan (40% by weight), inulin (31% by weight), and PROVON™ (16% by weight).

Example 2

Dietary Composition Formulation

A powder mix was formed by blending SLENDESTA™ (12% by weight), oat beta glucan (14% by weight), barley beta glucan (40% by weight), inulin (24% by weight), and PROVON™ (10% by weight). The oat and barley beta glucan were analyzed by gas chromatography to ensure the authenticity of the extracted compounds.

Example 3

Dietary Composition Formulation as a Meal Replacement Bar

A powder mix was formed by blending SLENDESTA™ (6% by weight), oat beta glucan (2% by weight), barley beta glucan (45% by weight), inulin (10% by weight), and PROVON™ (37% by weight). This blend was incorporated into a base of soy crisps, syrups, sweeteners, and fiber sources to produce an extruded protein bar. This bar can be about 50 grams in weight, and can provide one serving of pre-blend. The product can be coated or partially coated in chocolate (or other flavor), and each bar can be individually packaged. The final product can be consumed as one serving as either a meal replacement or snack item.

Example 4

Dietary Composition Formulation—Meal Replacement Shake

A powder mix was formed by blending SLENDESTA™ (4% by weight), oat beta glucan (2% by weight), barley beta glucan (7% by weight), inulin (12% by weight), and PROVON™ (75% by weight). This blend was added to a meal replacement shake base (including fructose, sunflower oil creamer, protein, and fiber sources to create a meal replacement shake that includes one serving of pre-blend). The final shake can be any flavor (e.g., chocolate, vanilla, or strawberry). Final serving size can be 30 g to be dispersed into 8 ounces of milk or water to form one complete serving.

OTHER EMBODIMENTS

It is to be understood that while the above embodiments have been described in conjunction with the detailed description thereof, the foregoing description is intended to illustrate, and not limit the scope of the inventive concepts, which are defined by the scope of the appended claims. Other aspects, advantages, and modifications are within the scope of the following claims.

What is claimed is:

1. A dietary composition comprising, per serving, from about 10 mg to about 750 mg of oat beta glucan, from about 10 mg to about 750 mg of barley beta glucan, from about 100 mg to about 10 g of whey protein isolate, from about 100 mg to about 600 mg of a natural protein extract derived from potatoes, and from about 100 mg up to about 7 g of inulin.

2. The dietary composition of claim 1, wherein the inulin is present from about 2 percent to about 50 percent by weight.

3. The dietary composition of claim 1, wherein the oat beta glucan is present from about 2 percent to about 50 percent by weight.

4. The dietary composition of claim 1, wherein the barley beta glucan is present from about 2 percent to about 50 percent by weight.

5. The dietary composition of claim 1, wherein the protein extract includes Proteinase Inhibitor II.

6. The dietary composition of claim 1, wherein the protein extract is present from about 2 percent to about 14 percent by weight.

7. The dietary composition of claim 1, wherein the whey protein isolate is present from about 5 percent to about 50 percent by weight.

8. The dietary composition of claim 1, wherein said dietary composition is a pill, a powder, or a liquid.

9. The dietary composition of claim 1, wherein said dietary composition is incorporated as part of a powdered shake mix.

10. The dietary composition of claim 1, wherein said dietary composition is incorporated as part of a protein bar.

11. A dietary composition consisting essentially of between 15 and 300 mg of potato protein extract, between 10 and 1250 mg of oat beta glucan, between 10 and 1250 mg of barley beta glucan, between 50 and 1250 mg of inulin, and between 125 and 1250 mg of a dairy protein source.

12. A dietary composition consisting essentially of between about 2 percent to about 14 percent by weight potato protein extract, 2 percent to about 50 percent by weight oat beta glucan, 2 percent to about 50 percent by weight barley beta glucan, 2 percent to about 50 percent by weight inulin, and 5 percent to about 50 percent by weight diary protein source.

13. The dietary composition of claim 12 consisting essentially of about 4 percent by weight potato protein extract, about 6 percent by weight potato protein extract, or about 12 percent by weight potato protein extract.

14. The dietary composition of claim 12 consisting essentially of about 2 percent by weight oat beta glucan, 7 percent by weight oat beta glucan, or 14 percent by weight oat beta glucan.

15. The dietary composition of claim 12 consisting essentially of about 7 percent by weight barley beta glucan, 40 percent by weight barley beta glucan, or 45 percent by weight barley beta glucan.

16. The dietary composition of claim 12 consisting essentially of about 10 percent by weight inulin, 12 percent by weight inulin, 24 percent by weight inulin, or 31 percent by weight inulin.

17. The dietary composition of claim 12 consisting essentially of about 10 percent by weight dairy protein source, 16 percent by weight dairy protein source, 37 percent by weight dairy protein source, or 75 percent by weight dairy protein source.

18. The dietary composition of claim 12, wherein the dairy protein source is whey protein isolate.

* * * * *